United States Patent
Fischer et al.

(10) Patent No.: US 7,168,951 B2
(45) Date of Patent: Jan. 30, 2007

(54) REINFORCED GINGIVAL RETRACTION CORD

(75) Inventors: Dan E. Fischer, Sandy, UT (US); Ammon Black, West Valley City, UT (US)

(73) Assignee: Ultradent Products, Inc., South Jordan, UT (US)

(*) Notice: Subject to any disclaimer, the term of this patent is extended or adjusted under 35 U.S.C. 154(b) by 0 days.

(21) Appl. No.: 11/064,725

(22) Filed: Feb. 24, 2005

(65) Prior Publication Data

US 2005/0277088 A1 Dec. 15, 2005

Related U.S. Application Data

(63) Continuation-in-part of application No. 10/863,974, filed on Jun. 9, 2004, now Pat. No. 7,121,828.

(51) Int. Cl.
*A61C 5/14* (2006.01)

(52) U.S. Cl. .................................................. 433/136

(58) Field of Classification Search ................ 433/136, 433/138–139, 215
See application file for complete search history.

(56) References Cited

U.S. PATENT DOCUMENTS

| | | | |
|---|---|---|---|
| 4,321,038 A | 3/1982 | Porteous | 433/136 |
| 4,465,462 A | 8/1984 | Ticknor | 433/136 |
| 4,522,593 A | 6/1985 | Fischer | 433/136 |
| 4,617,950 A | 10/1986 | Porteous et al. | 132/91 |
| 4,871,311 A | 10/1989 | Hagne | 433/136 |
| 4,892,482 A | 1/1990 | Lococo | 433/136 |
| 5,022,859 A | 6/1991 | Oliva | 433/141 |
| 5,540,588 A | 7/1996 | Earle | 433/136 |
| 5,676,543 A | 10/1997 | Dragan | 433/136 |
| 5,899,694 A | 5/1999 | Summer | 433/136 |
| 6,375,461 B1 | 4/2002 | Jensen et al. | 433/136 |
| 6,612,839 B2 | 9/2003 | Loynes | 433/136 |

FOREIGN PATENT DOCUMENTS

JP 1139057 5/1989

OTHER PUBLICATIONS

Fazekas, A., "Effects of Pre-Soaked Retraction Cords on the Microcirculation of the Human Gingival Margin" Oper Dent 27(4): 343-8 2002.
Nieto-Martinez, D., "Effects of Diameter, Chemical Impregnation and Hydration on the Tensile Strength of Gingival Retraction Cords" J. Oral Rehibil, 28(12): 1094-100 2002.
O'Mahony A., "Effect of 3 Medicaments on the Dimensional Accuracy and Surface Detail Reproduction of Polyvinyl Siloxane Impressions" Quintessence Int., 31(3): 201-6 2001.
Donovan, T.E., "Review and Survey of Medicaments Used With Gingival Retraction Cords" J. Prosthet Dent, 53(4): 525-31 1985.

*Primary Examiner*—John J Wilson
(74) *Attorney, Agent, or Firm*—Workman Nydegger

(57) ABSTRACT

Gingival retraction cords are constructed from two or more strands that are interlocked to form a knitted, braided, woven, or twisted retraction cord. At least one strand is made from an absorbent material and another strand is made from a degradation-resistant material, such as nylon, polyester, fiberglass, or metal. The absorbent strands are impregnated with an active agent. The degradation-resistant strands resist degradation by the active agent. Alternatively, one or more strands are used to make the knit, weave, or braid and each strand is made from two or more different fibers. For example, one or more absorbent fibers and one or more synthetic fibers can be twisted to make a blended strand. The blended strands can be used to knit, braid, or weave a retraction cord. Because the degradation-resistant strands are part of the strand pattern, the retraction cords can be made sturdier without adversely affecting the cord's inherent deformation properties.

5 Claims, 3 Drawing Sheets

REINFORCED GINGIVAL RETRACTION CORD

CROSS-REFERENCE TO RELATED APPLICATIONS

This application is a continuation-in-part of U.S. application Ser. No. 10/863,974, entitled "Reinforced Gingival Retraction Cord," filed Jun. 9, 2004, now U.S. Pat. No. 7,121,828 the disclosure of which is incorporated in its entirety.

BACKGROUND OF THE INVENTION

1. The Field of the Invention

The present invention relates to gingival retraction cords. More particularly, the present invention relates to chemically impregnated retraction cords that have an additional strand or fiber incorporated therein for reinforcing or enhancing the cord.

2. The Related Technology

When performing various dental procedures, it is often desirable to retract the gingival tissue to prepare the patient's teeth for the procedure. Taking dental impressions, placing crowns, performing bridge work, or effecting other dental restorations are examples of procedures that benefit from retracted gingival tissue. A widely used method for retracting gingival tissue involves the use of retraction cords which are typically braided or knitted for increased strength, flexibility and resilience. Examples of braided or knitted gingival retraction cords may be found in U.S. Pat. No. 4,321,038 to Porteous, U.S. Pat. No. 4,522,933 to Fischer, U.S. Pat. No. 4,617,950 to Porteous et al., and U.S. Pat. No. 4,892,482 to Lococo.

The most common purpose for using a retraction cord is to retract the gingiva away from the tooth to take an accurate and reliable impression of the tooth. It is important to make an accurate impression of the tooth when constructing artificial crowns to ensure that the crown remains properly secured to the tooth for an extended period of time. It is particularly important to make an accurate impression of the tooth in the area at or below the gingival margin. Failure to take an accurate impression can result in a poorly-formed or deficient prosthesis, particularly at the gingival margin. Premature failure of a crown is often due to poor marginal detail in the impression used to fabricate the crown.

The person's gingiva, or "gums", not only prevents an accurate impression of the proper shape of a person's tooth beneath the gingiva, it may also bleed if torn or damaged by high speed cutting drills or burrs used to remove tooth material preparatory to placing a crown. This bleeding may further interfere with the taking of a good impression because extravasated blood tends to prevent adequate cleaning and drying of the marginal area of the tooth prior to taking an impression and tends to displace the impression material before it can set. Thus, the dual problems of contraction of the gingival cuff and the presence of hemorrhaging tissues make it impractical to simply take an impression following shaping of the tooth with a high speed drill or burr without retraction of the gingiva.

To control or inhibit the tendency of the gingiva to bleed when physically retracted by the retraction cord and/or if accidentally cut or nicked by the high speed drill or burr, retraction cords are often treated with a hemostatic agent. One type of hemostatic agent includes astringents, which lock or seal off exposed blood vessels so as to arrest bleeding. U.S. Pat. Nos. 4,321,038, 4,522,933, 4,617,950 and 4,892,482, referred to above, discuss the use of astringents such as "alum", or potassium aluminum sulfate.

Many chemicals used to impregnate a retraction cord often have an adverse affect on the strength of the fibers in the retraction cord. Many retraction cords are made of knitted or braided cotton fibers. The hemostatic agent or astringent placed in the retraction cord can degrade the cord over time making it more likely to fail during use. If fibers in the knit or braid fail during use, the dental packing instrument used to insert the retraction cord into the sulcus can slip through the fibers and potentially cut or injure the underlying tissue. In addition, fragments of the retraction cord can remain embedded between the tooth and gums. Furthermore, the expandability and resilience of the retraction cord diminishes as the integrity of the knit or weave of the cord degrades.

Therefore, what is needed is a gingival retraction cord that can properly retract the gingiva using a hemostatic agent while also resisting degradation due to the hemostatic agent.

BRIEF SUMMARY OF THE INVENTION

The present invention overcomes the above-mentioned problems in the prior art by providing a gingival retraction cord that resists degradation when impregnated with an active agent such as a hemostatic agent. According to one embodiment of the present invention, a retraction cord is formed by interlocking two or more strands so as to form a knitted, braided, woven, or twisted retraction cord. At least one of the strands is made from an absorbent material such as cotton. The absorbent strand is impregnated with an active agent such as a hemostat.

At least one other strand in the, knitted, braided or woven pattern is made from a degradation-resistant fiber such as a polymer, ceramic, or carbon-based material. The degradation-resistant strand provides the retraction cord with additional structural integrity by resisting degradation caused by one or more active agents. In one embodiment, the degradation-resistant strand comprises a thin metallic filament such as silver having a thickness less than 0.2 mm.

In an alternative embodiment, the retraction cord of the present invention is formed from one or more strands made from a blend of fibers. One or more absorbent fibers can be twisted together with one or more types of degradation resistant fibers to form one or more reinforced blended strands. The blended strands are then knitted, braided, woven, or twisted to form the retraction cord of the present invention. In this particular embodiment, each strand of the knit, braid, or weave can advantageously include one or more types of degradation-resistant fibers such that the entire retraction cord resists degradation.

The retraction cord of the present invention may be impregnated with an active agent such as potassium aluminum sulfate, aluminum ammonium sulfate, aluminum sulfate, aluminum chlorohydrate, aluminum acetate, ferric sulfate, ferric subsulfate, ferric chloride, and mixtures thereof. The absorbent strand acts as a carrier for a solution of the active agent. When the retraction cord is packed into the sulcus between the gingiva and a tooth, the active agent is released into the tissue where it arrests bleeding or stiffens the gingival tissue.

The degradation-resistant strand gives the retraction cord durability in the presence of a hemostatic agent or other corrosive material. As the hemostatic agent breaks down other strands or fibers, the degradation resistant strand resists such degradation thereby preserving the structural integrity of the cord.

The different strands and/or fibers used to make the retraction cord of the present invention are blended together such that each fiber or strand follows the knit, braid, or weave pattern. In this way, the blending does not compromise the beneficial features of the braid or weave pattern. Thus, blends of absorbent and degradation-resistant strands or fibers can provide the retraction cord with beneficial characteristics without compromising the benefits derived from the braid or weave pattern.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF EXEMPLARY EMBODIMENTS

I. Retraction Cords

As used herein, the terms "knitting" and "knitted" relate to a process of using one or more separate strands to form a series of interlocking loops. A "strand" may include one or more fibers which are twisted or otherwise joined together.

A. Strand Pattern

Retraction cords according to the present invention can be made using any of various techniques, including knitting, braiding, weaving, or twisting.

Figure 1:
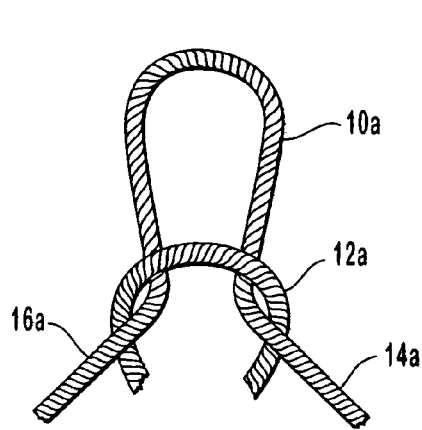
FIG. 1 illustrates an open-loop configuration used in knitting.
Figure 2:
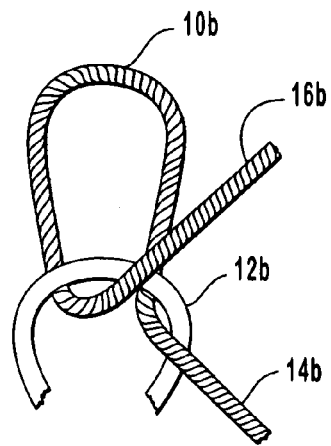
FIG. 2 illustrates a closed-loop configuration used in knitting.

As shown in FIGS. 1 and 2, two common types of knitting techniques that can be used to form the retraction cords of the present invention include knits made from an "open" loop and a "closed loop." The "open" loop shown in FIG. 1 is formed using a first loop 10a that is interlocked with an adjacent loop 12a such that ends 14a and 16a of loop 10a do not cross one another.

In contrast, FIG. 2 illustrates what is generally known as a "closed" loop knit. The end 16b of first loop 10b bends back over and crosses in a manner that closes off the loop 10b.

Figure 3:
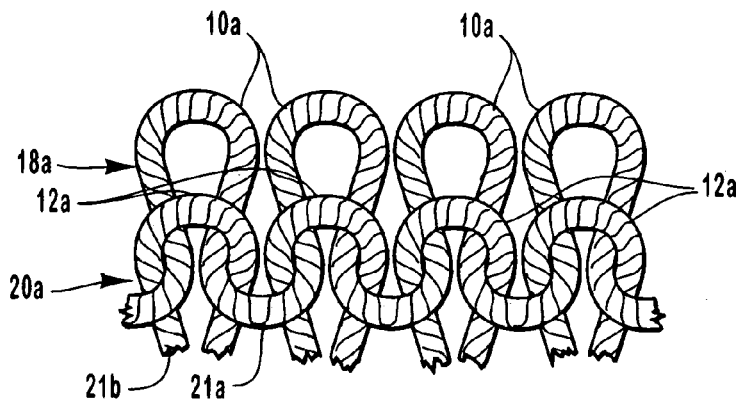
FIG. 3 schematically illustrates the manner in which a single strand of yarn can be knitted using the open-loop configuration of FIG. 1 so as to form a knitted retraction cord from a single strand.

FIG. 3 illustrates two rows (generally designated at 18a and 20a) of interlocked loops constructed utilizing the open-loop configuration shown in FIG. 1. As seen in FIG. 3, row 18a includes a plurality of loops 10a, which are interlocked with loops 12a of adjacent row 20a. FIG. 3 illustrates "weft" knitting, which is made from one loop to the next in the same course, or row, of loops, and which can be done using a first strand 21a for row 18a and a second strand 21b for row 20a. Alternatively, weft knitting can be performed using a single strand or more than 2 strands.

As discussed more fully below, strands 21a and 21b are a blend or can include a blend of different materials to give the retraction cord beneficial properties such as resistance to the degrading effects of a hemostatic agent or other corrosive material.

Figure 4:
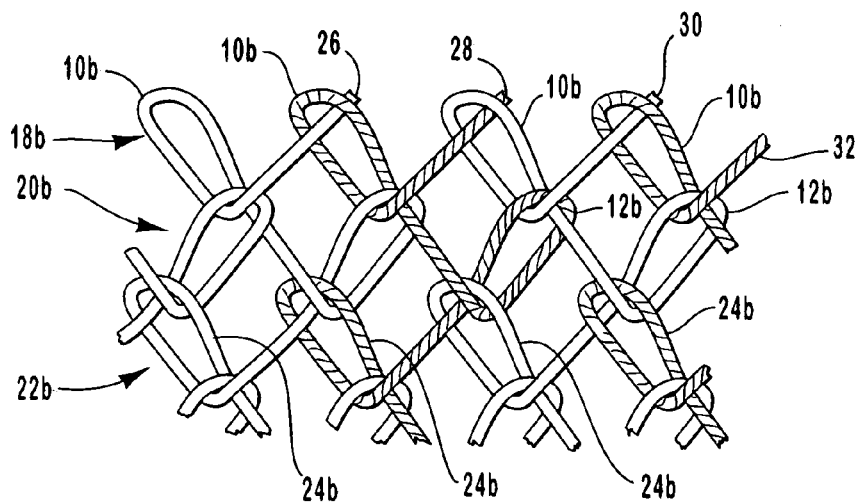
FIG. 4 schematically illustrates the manner in which a plurality of strands may be interlocked and knitted using the closed-loop configuration of FIG. 2 so as to form a knitted retraction cord from several strands.

FIG. 4, alternatively, illustrates three rows (generally designated at 18b, 20b, and 22b, respectively) of interlocked loops constructed utilizing the closed-loop configuration of FIG. 2. As seen in FIG. 4, row 18b includes loops 10b, which are interlocked with the loops 12b of adjacent row 20b. Loops 12b of row 20b are in turn interlocked with the loops 24b of adjacent row 22b, and so on.

FIG. 4 illustrates "warp" knitting in which several strands 26, 28, 30, and 32, are interconnected such that the interlocking loops of each strand connect from one row to the next. As discussed more fully below, the knitted strands can be made of one or more different materials to give the retraction cord advantageous properties.

Figure 5:
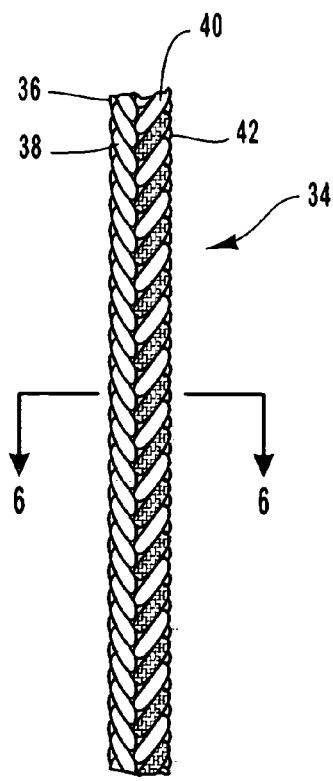
FIG. 5 illustrates a length of knitted retraction cord formed from four strands according to an exemplary embodiment of the present invention, in which one strand is made from a synthetic material.

FIG. 5 shows a gingival retraction cord 34 knitted from four strands 36, 38, 40, and 42 using the closed-loop pattern shown in FIGS. 2 and 4. The number and pattern of strands 36, 38, 40, and 42 is more readily apparent in the cross sectional view of retraction cord 34 illustrated in FIG. 6.

It will be appreciated that the knitted retraction cord of the present invention can be constructed using either an open-loop or a closed-loop pattern or system, as shown in FIGS. 1–5. Retraction cord 34 can also be made using other kitting patterns so long as the knit pattern provides sufficient elasticity and/or resilience. Furthermore, those skilled in the art will recognize that the knit pattern can include any number of strands and each strand can be made from any number of fibers.

In another embodiment of the present invention, the two or more strands are interlocked to form a braided, woven, or twisted retraction cord.

Figure 9:
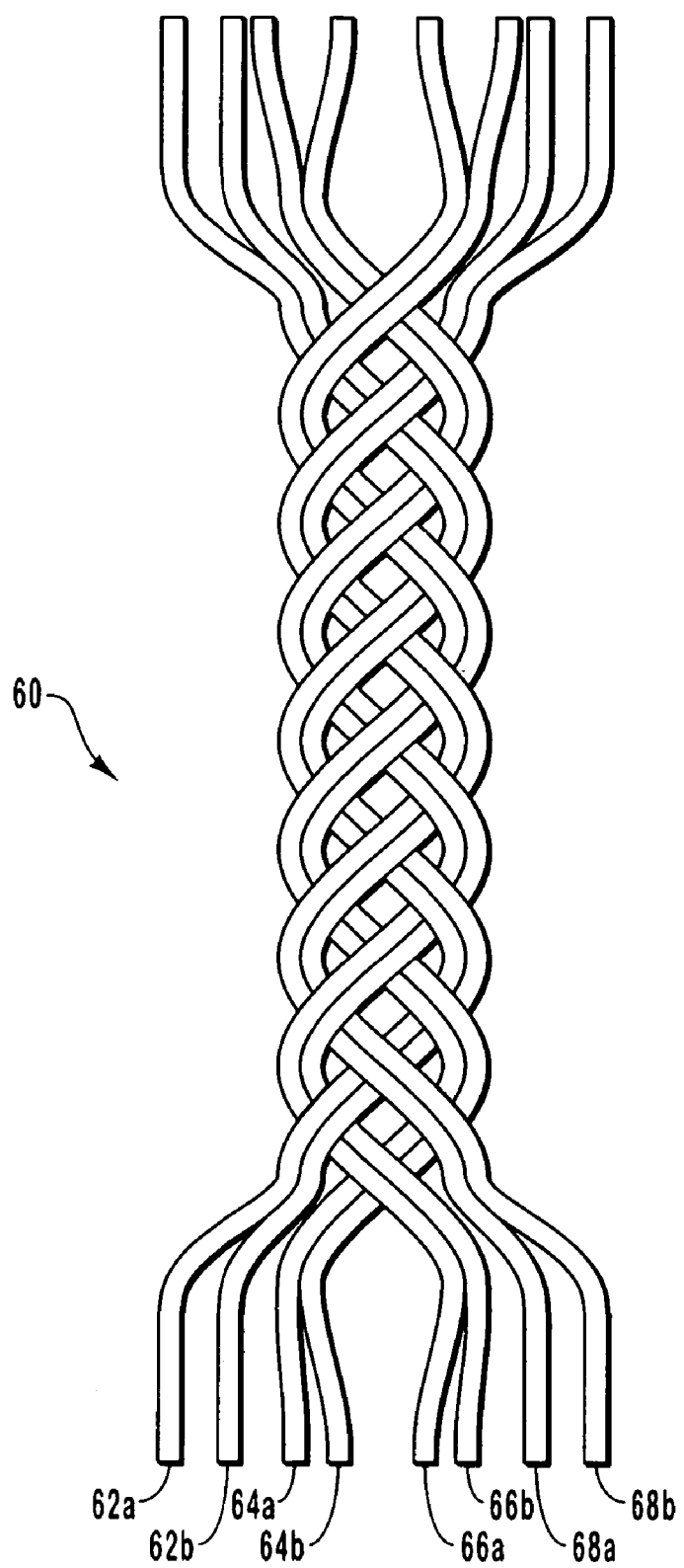
FIG. 9 illustrates an exemplary retraction cord formed using several strands in a braided pattern.

FIG. 9 illustrates an exemplary braided cord 60. Braided cord 60 has four pairs of strands 62, 64, 66, and 68, which each include an "a" strand and a "b" strand. The braid is formed by taking the leftmost strand pair and passing it under over and then under successive strands to the right. To illustrate this pattern, the braid in FIG. 9 would be continued by taking strand pair 62 (i.e. strands 62a and 62b) and passing it under strand pair 64, over strand pair 66 and under strand pair 68. Following this series of interlocking strands, strand pair 64 would be the left most strand pair. Continuing the braid even further would entail passing strand pair 64 under strand pair 66, over strand pair 68 and under strand pair 62, and so forth to form the braid having interlocking strands.

The braided cords of the present invention can include any number of strands that are interlocked to form the braid. Furthermore, the strands that are interlocked to form the braid can be pairs of strands as in FIG. 9, or can be single strands or have more than two strands.

The present invention can be carried out using other configurations of strands. For example, two or more strands can be placed adjacent each other and then twisted to interlock the strands to form a twisted cord. In another embodiment, two or more strands can be interlocked to form a weave. Those skilled in the art are familiar with the different types of braids and weaves that can be used to form a retraction cord.

B. Strands and/or Fiber Blends

Figure 6:
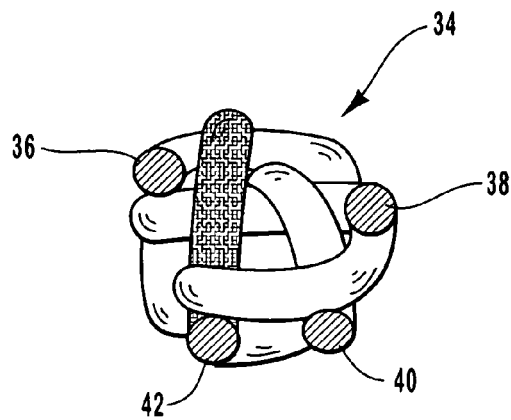
FIG. 6 illustrates a transverse cross-section of the knitted retraction cord of FIG. 5 taken along line 6—6.

With continued reference to FIGS. 5 and 6, strands 36, 38, 40, and 42 are a blend of strand materials. In an exemplary embodiment, strands 36, 38, and 40 are cotton strands and strand 42 is a synthetic polymer such as nylon or polyester. Alternatively, strand 42 can be a ceramic, carbon-based, or thin metallic strand having a thickness less than about 2 mm. The blended strands are knitted to form retraction cord 34 having a 3:1 ratio of absorbent to degradation-resistant strands. The blend can be adjusted as desired by using more or fewer absorbent and/or degradation-resistant strands.

It is particularly useful for metallic strands to have a thickness less than 0.2 mm, although other degradation-resistant strands can also have thickness less than 0.2 mm, in order for the metallic filament to retain high flexibility for increased comfort and ease of placement of the retraction cord. Metallic wires having a thickness of 0.2 mm or more tend to be overly stiff. To ensure that metallic or other filaments have a high level of flexibility, such filaments will preferably have a thickness less than about 0.15 mm, more preferably less than about 0.1 mm; and most preferably less than about 0.075 mm.

Figure 7:
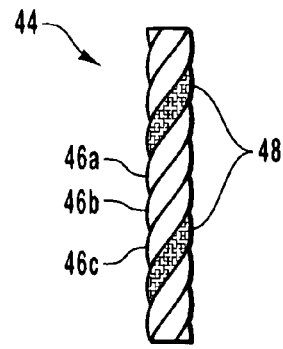
FIG. 7 illustrates an alternative embodiment of the present invention showing a single strand of the knit being made from a blend of fibers.

In another embodiment, a blended cord material is created by blending two or more fibers to make a strand. One or more strands having blended fibers are then knitted to make a retraction cord. FIG. 7 illustrates an exemplary strand 44 that is made from a blend of cotton fibers 46a–46c and a synthetic fiber 48. Fibers 46a–46c and fiber 48 are twisted together to form strand 44 having a 3:1 ratio of absorbent to degradation-resistant fibers.

It will be appreciated that strands can be made from more or fewer absorbent fibers and/or degradation-resistant fibers such that the retraction cords of the present invention can have almost any desired blend ratio. Furthermore, blended strands can also be blended with other blended or non-blended strands to create a retraction cord having a desired absorption, resistance to degradation, or resiliency.

Materials used to create the blends of the present invention include natural and synthetic polymers, coated polymers, metal filaments, or any other threadable material that can give the retraction cord a desired property. For instance, cotton can be used for its absorbency, low cost, and biocompatibility. In one embodiment a polymer fiber or metal filament can be selected to give the refraction cord a desired resiliency, elasticity, or deformability. A metal filament such as silver can also be included to make the retraction cord radiopaque. Other suitable materials include eaton fibers and filaments and ceramic fibers (e.g., fiberglass).

In an exemplary embodiment, a synthetic polymer such as nylon or polyester is included in the knit of the retraction cord to resist degradation by an active agent. As discussed below, active agents such as hemostatic agents can be included in the retraction cord of the present invention to assist in controlling bleeding of the gingival during a procedure. Active agents that are corrosive can break down absorbent fibers such as cotton. In accordance with one embodiment of the present invention, a synthetic polymer such as nylon or polyester is included in the knit to resist degradation and thus failure of the retraction cord. Preventing the failure of the knit helps ensure that the retraction cord properly retracts gingival tissue and reduces the chances that a packing instrument will pierce the knit of the cord and damage the underlying tissue.

As mentioned above, the non-degrading fiber or filament can be blended into the knit through a strand or through individual fibers. In this regard, it can be advantageous to include the non-degrading material as a fiber in each strand of the knit. In this manner, each strand is structurally supported and improved by the blend of fibers.

Similar to the knitted retraction cords, retraction cords made using a braid, weave, twist, or other strand pattern can have any number or combination of strands in the strand pattern. In addition, the braid, weave, or twist may have individual strands with combinations of different fibers, similar to the combinations illustrated in FIG. 7, for example.

Referring again to FIG. 9, in one embodiment, one or more of the pairs of strands 62, 64, 66, and 68 includes an absorbent strand and a degradation-resistant strand. For example, 62a can comprise a degradation-resistant strand and 62b can comprise an absorbent strand such as cotton.

In an alternative embodiment, one or more of the individual strands of strand pairs 62, 64, 66, and 68 has fibers that include an absorbent fiber and/or a degradation-resistant fiber.

In yet another embodiment, the degradation-resistant strand and the absorbent strands are different, pairs of interlocking strands. For example, both strands 64a and 64b can be made from an absorbent material such as cotton and strands 66a and 66b can be made from a degradation-resistant strand such as a polymer.

The retraction cords of the present invention are designed to obtain the benefit of having various different materials in the cord, without destroying the benefits of the particular strand pattern. Knitted, braided, woven, and twisted cords all, have certain flexibility, resilience, and packing properties. Unlike attempts in the prior art, the blends of the present invention do not prevent the natural movements of the cord because the degradation-resistant strands and the absorbent strands form part of the knit, weave, twist, or braid and are flexible.

II. Active Agents

In an exemplary embodiment, the retraction cord of the present invention includes an active agent such as a hemostatic agent. Hemostatic agents, including astringents and other vasoconstrictors, can be impregnated in the retraction cord to control bleeding and stiffen gingival tissue.

Active agents that may be useful in assisting hemostasis include, but are not limited to aluminum compounds such as potassium aluminum sulfate, aluminum ammonium sulfate, aluminum sulfate, aluminum chlorohydrate, aluminum acetate, other water soluble astringent aluminum salts, and mixtures thereof. Another class of astringents includes iron-based compositions such as ferric salts, including but not limited to ferric sulfate, ferric subsulfate, ferric chloride, and mixtures thereof. Other astringents include permanganates, tannins and zinc chloride. In one embodiment the active agent is a vasoconstrictor such as epinephrine and/or propylhexedrine.

The active agent is typically delivered to the gingival tissue in a solution, such as an aqueous solution. As discussed above, in an exemplary embodiment, retraction cord 34 includes an absorbent material. The absorbent material absorbs the solution thereby impregnating the retraction cord 34 with the active agent. While the active agent may be impregnated using a mechanism other than a solution, a solution is beneficial because it can easily be expressed in the sulcus.

The knitted pattern of retraction cord 34 helps absorb and deliver the active agent. The interlocking loops of the knit pattern substantially increase interstitial a volume of cord 34, which allows the retraction cord to carry larger amounts of active agent. Because the knit pattern carries additional active agent, non-absorbent strands can be blended into the knit pattern without affecting the hemostatic ability of the retraction cord.

Additionally, the ability of knitted retraction cords to effectively deliver the active agents to the gingival tissue is greatly augmented by the fact that the knitted retraction cords are compressed when packed in the sulcus. Thus, knitted cords may actually express the hemostatic or other active agent(s) into the small capillaries of the gingival tissue when compressed, thereby forcing the active agents into the bleeding pores so as to stop hemorrhage.

III. Method of Use

Figure 8:
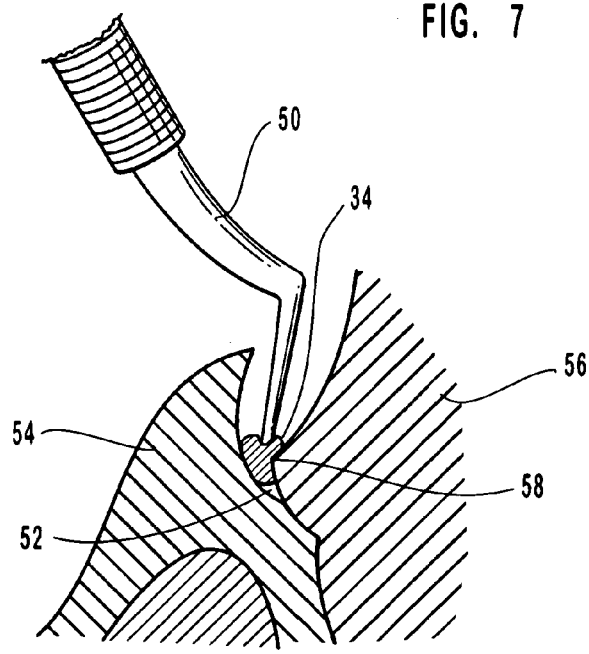
FIG. 8 schematically illustrates a cross-sectional portion of a tooth, the tooth's associated gingival cuff, and a knitted retraction cord being packed into the gingival sulcus between the tooth and the gingival cuff.

In FIG. 8, a dental instrument 50 is shown pressing the gingival retraction cord 34 within the sulcus 52 between the gingival cuff 54 and the tooth 56. The resilience and flexibility in the transverse direction allows the knitted retraction cord 34 to conform to irregularities, such as the margin 58 of the tooth 56.

Even if the loops of the knitted retraction cord are left rather loose, because of the intricate interlocking network, there is little or no tendency for the dental packing instrument to slip through the retraction cord. Rather, the compressibility of the knitted cord 34 causes the cord 34 to "dimple" around the edges of the dental packing instrument 50.

Because of the compressibility and bendability of knitted retraction cords there is less of a tendency for the cords to damage underlying gingival tissue as force is applied during packing. This is because the force of the packing instrument tends to be spread out over a larger area by the interlocking loops of the knitted cord. Also, the transverse resilience of the knitted cord enables it to conform to irregularities within the sulcus. Thus, the knitted cord can accomplish both horizontal and vertical retraction using a single cord.

Another advantage of knitted retraction cords is their tendency to return to their original, uncompressed shape because of their resilience. Thus, when a knitted retraction cord is packed into the sulcus, it is compressed, and the "memory" in the retraction cord causes the cord to gently push outward against the gingival tissue 54. This outward pushing increases the ability of the knitted cord 34 to retract gingival tissues over conventional retraction cords.

Another advantage arising from the compressibility of knitted retraction cords is realized when retracting gingival tissue around the front teeth. The labial gingival tissue is particularly thin and membranous as compared to the lingual gingival tissue. Using the knitted retraction cords of the present invention the lingual gingival tissue can be adequately retracted with the knitted retraction cord only slightly compressed, and by virtue of its compressibility and its ability to stretch and become thinner, the same cord can be packed into the sulcus on the labial side of an interior tooth without over-retracting the gingival tissue. The cord then exerts a general, steady outward force on the tissue, which is desirable.

Another feature of the retraction cord of the present invention is that it can be chemically impregnated with an active agent over an extended period of time without compromising the knit pattern and the benefits that accompany a knitted cord. The degradation-resistant fibers or strands blended into the knit of the retraction cord permit chemical impregnation yet give the retraction cord strength in the event that the active agent degrades other fibers in the cord.

While there are many benefits for using a knitted cord, in some cases, braided, woven, or twisted retraction cords can be preferred. This preference can be because of the cost to manufacture a particular cord, or because of the experience that a practitioner may have with a particular type of retraction cord. In any event, braided, woven, and twisted cords are improved by including a combination of an absorbent strand and a degradation-resistant strand according to the present invention.

The braided, woven, or twisted retraction cords of the present invention benefit from having the degradation resistant strands or fibers used in the braid, weave, or twisted pattern. The braided, woven, or twisted retraction cords bend and pack in a manner that is typical of the particular strand pattern type. Thus, the retraction cord bending and packing properties are not substantially affected by the inclusion of the degradation resistant strands. Furthermore, the braided, woven, or twisted retraction cords can be impregnated with an active agent and resist degradation of the cord by the active agent.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A gingival retraction cord, comprising:
    at least one absorbent strand and at least one flexible degradation-resistant strand interlocked so as to form a braided, woven, or twisted retraction cord that is flexible, wherein the flexible degradation-resistant strand has a thickness less than 0.2 mm; and
    wherein the absorbent strand is entirely comprised of fibers that are absorbent; and
    wherein the degradation resistant strand is entirely comprised of synthetic fibers that are degradation-resistant; and
    an active agent impregnated within the absorbent strand of the retraction cord, wherein the degradation-resistant strand resists degradation by the active agent.

2. A gingival retraction cord as in claim 1, wherein the flexible degradation-resistant strand has a thickness less than about 0.15 mm.

3. A gingival retraction cord as in claim 1, wherein the flexible degradation-resistant strand has a thickness less than about 0.1 mm.

4. A gingival retraction cord as in claim 1, wherein the flexible degradation-resistant strand has a thickness less than about 0.075 mm.

5. A gingival retraction cord as in claim 1, wherein the active agent comprises a hemostatic agent selected from the group consisting of potassium aluminum sulfate, aluminum ammonium sulfate, aluminum sulfate, aluminum chlorohydrate, aluminum acetate, ferric sulfate, ferric sub sulfate, ferric chloride, and mixtures thereof.

* * * * *

UNITED STATES PATENT AND TRADEMARK OFFICE
CERTIFICATE OF CORRECTION

PATENT NO. : 7,168,951 B2 Page 1 of 1
APPLICATION NO. : 11/064725
DATED : January 30, 2007
INVENTOR(S) : Fischer et al.

It is certified that error appears in the above-identified patent and that said Letters Patent is hereby corrected as shown below:

Column 2
Line 4, change "affect" to --effect--
Line 33, change "the," to --the--

Column 4
Line 48, change "kitting" to --knitting--

Column 5
Line 60, change "eaton" to --carbon--

Column 6
Line 32, change "different," to --different--
Line 40, change "all," to --all--

Column 7
Line 7, remove "a"

Signed and Sealed this

Second Day of September, 2008

JON W. DUDAS
*Director of the United States Patent and Trademark Office*

UNITED STATES PATENT AND TRADEMARK OFFICE
CERTIFICATE OF CORRECTION

PATENT NO.        : 7,168,951 B2                                    Page 1 of 1
APPLICATION NO.   : 11/064725
DATED             : January 30, 2007
INVENTOR(S)       : Fischer et al.

It is certified that error appears in the above-identified patent and that said Letters Patent is hereby corrected as shown below:

Column 2
Line 4, change "affect" to --effect--
Line 33, change "the," to --the--

Column 4
Line 48, change "kitting" to --knitting--

Column 5
Line 60, change "eaton" to --carbon--

Column 6
Line 32, change "different," to --different--
Line 40, change "all," to --all--

Column 7
Line 7, remove "a"

Signed and Sealed this

Ninth Day of September, 2008

JON W. DUDAS
*Director of the United States Patent and Trademark Office*